United States Patent
Weast

(10) Patent No.: US 7,104,627 B2
(45) Date of Patent: Sep. 12, 2006

(54) VARYING PRINTING SPEED BASED UPON THE DIFFERENTIATION BETWEEN POROUS AND SWELLABLE MEDIA VIA INK/TONER DRY TIME PROFILES

(75) Inventor: Aaron B. Weast, Camas, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 241 days.

(21) Appl. No.: 10/915,970

(22) Filed: Aug. 11, 2004

(65) Prior Publication Data

US 2006/0033767 A1    Feb. 16, 2006

(51) Int. Cl.
B41J 29/393    (2006.01)
(52) U.S. Cl. .......................................... 347/19
(58) Field of Classification Search ................ 347/109, 347/105
See application file for complete search history.

(56) References Cited

U.S. PATENT DOCUMENTS

| | | | |
|---|---|---|---|
| 5,764,251 A | 6/1998 | Hashimoto | |
| 5,784,090 A | 7/1998 | Selensky et al. | |
| 6,109,723 A | 8/2000 | Castle et al. | |
| 6,132,021 A | 10/2000 | Smith et al. | |
| 6,149,327 A | 11/2000 | Ward et al. | |
| 6,184,991 B1 | 2/2001 | Soto et al. | |
| 6,457,801 B1 | 10/2002 | Fish et al. | |
| 6,523,920 B1 | 2/2003 | Wade et al. | |
| 6,568,780 B1 | 5/2003 | Schantz et al. | |
| 6,685,313 B1 * | 2/2004 | Scofield et al. ............. | 347/105 |
| 6,731,393 B1 * | 5/2004 | Currans et al. ............ | 358/1.12 |
| 6,900,449 B1 * | 5/2005 | Bolash et al. .......... | 250/559.16 |
| 2001/0007458 A1 | 7/2001 | Purcell et al. | |
| 2002/0101469 A1 | 8/2002 | Wade et al. | |
| 2003/0020773 A1 | 1/2003 | Schantz et al. | |
| 2003/0025092 A1 | 2/2003 | Barnes | |
| 2003/0103103 A1 | 6/2003 | Smith | |

* cited by examiner

*Primary Examiner*—Lamson Nguyen
(74) *Attorney, Agent, or Firm*—James R. McDaniel

(57) ABSTRACT

This invention relates to a method for varying a printing speed based upon ink/toner dry time profiles, comprising the steps of: determining a gloss reading of an ink/toner located on a media; determining an actual ink/toner dry time profile for the media; determining the type of media; and adjusting, if possible, a printing speed of a printing device that is utilizing the ink/toner.

12 Claims, 2 Drawing Sheets

VARYING PRINTING SPEED BASED UPON THE DIFFERENTIATION BETWEEN POROUS AND SWELLABLE MEDIA VIA INK/TONER DRY TIME PROFILES

BACKGROUND OF THE INVENTION

1. Field of the Invention

This invention relates to a method for varying a printing speed based upon ink/toner dry time profiles, comprising the steps of: determining a gloss reading of an ink/toner located on a media; determining an actual ink/toner dry time profile for the media; determining the type of media; and adjusting, if possible, a printing speed of a printing device that is utilizing the ink/toner.

2. Description of the Related Art

Prior to the present invention, as set forth in general terms above and more specifically below, it is known, in the media sensing art to employ a media detection system that is capable of determining the media properties. Examples of this art include a variety of mechanical, electromechanical, and/or optical devices. While these devices are capable of determining the properties of the media, these devices do not measure the speed in which the ink/toner dries on the media so that a determination of the media type can be made based upon the ink/toner dry time profiles.

It is also known, in the media arts, to mark or otherwise encode the media so that the media type can be determined. Examples of this art include placing marks or other readable indicators directly upon the media to be printed. Also, marks or other readable indicators can be placed upon the packaging in which the media is located. While this media marking provides an adequate method for determining what type of media is being used, these methods do not measure the speed in which the ink/toner dries on the media so that a determination of the media type can we made based upon the ink/toner dry time profiles.

Finally, it is known, in the ink/toner arts, to measure the dry times of ink/toner in order to establish ink/toner dry time profiles. Typically, these profiles are then used to provide feedback to the user and/or printing device so that ink/toner will be given adequate time to dry or else it might smear or otherwise become illegible. While these systems provide an adequate method for determining the ink/toner dry time profiles, these systems do not utilize the dry time profiles in order to vary the printing speed based upon a determination of the media type.

It is apparent from the above that there exists a need in the media detection art for a media detection system which is capable of determining the media type based upon ink/toner dry time profiles, but which at the same time can alter the printing speed of the printing device based upon the type of media located in the printing device. It is a purpose of this invention to fulfill this and other needs in the art in a manner more apparent to the skilled artisan once given the following disclosure.

SUMMARY OF THE INVENTION

Generally speaking, an embodiment of this invention fulfills these needs by providing a method for varying a printing speed based upon ink/toner dry time profiles, comprising the steps of: determining a gloss reading of an ink/toner located on a media; determining an actual ink/toner dry time profile for the media; determining the type of media; and adjusting, if possible, a printing speed of a printing device that is utilizing the ink/toner.

In certain preferred embodiments, the method further includes the steps of determining an initial gloss reading of the media, printing upon the media, and determining an area upon the media in which the ink/toner can be detected and its gloss reading can be obtained.

In another further preferred embodiment, the printing speed of the printing device can be adjusted based upon the media being printed upon through the use a media type determination that is utilizing ink/toner dry time profiles.

The preferred method for varying a printing speed based upon ink/toner dry time profiles, according to various embodiments of the present invention, offers the following advantages: lightness in weight; ease of assembly and repair; excellent gloss reading characteristics; good stability; good durability; excellent media determination characteristics; excellent economy; and improved printing speed. In fact, in many of the preferred embodiments, these factors of excellent economy, excellent gloss reading characteristics, excellent media determination characteristics, and improved printing speed are optimized to an extent that is considerably higher than heretofore achieved in prior, known methods for varying a printing speed based upon ink/toner dry time profiles.

The above and other features of the present invention, which will become more apparent as the description proceeds, are best understood by considering the following detailed description in conjunction with the accompanying drawings, wherein like characters represent like parts throughout the several views and in which:

DETAILED DESCRIPTION OF THE INVENTION

Figure 1:
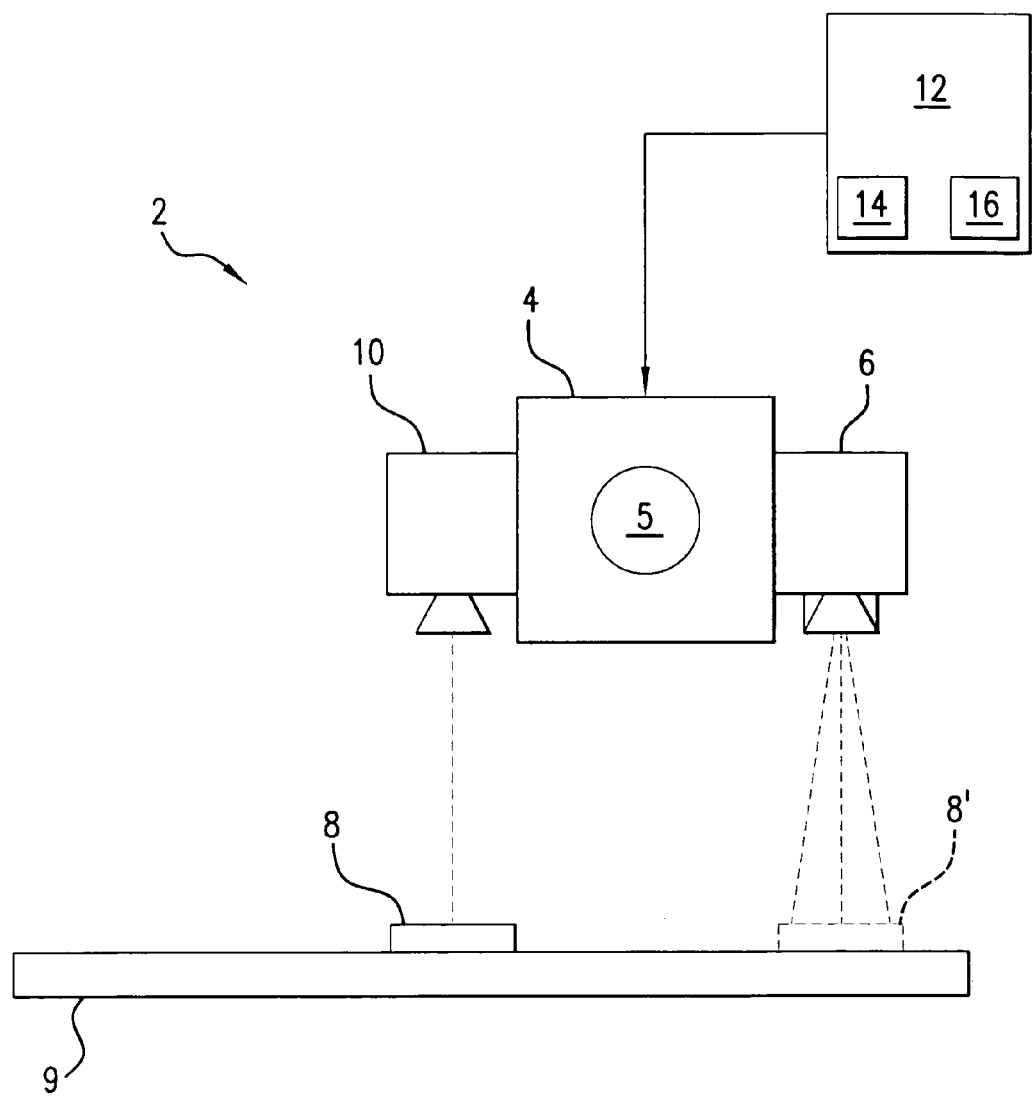
FIG. 1 is a schematic illustration of a system for varying printing speed based upon ink/toner dry time profiles, according to one embodiment of the present invention.

With reference first to FIG. 1, there is illustrated one preferred embodiment for use of the concepts of this invention. FIG. 1 schematically illustrates an apparatus 2 for varying printing speed of a printing device based upon ink/toner dry time profiles. Apparatus 2 includes, in part, printer carriage 4, conventional carriage rail 5, printer ink jet 6, ink/toner spots 8 and 8', media 9, ink/toner spot sensor 10, printer controller 12, printer speed controller 14, and ink/toner dry time profile registry 16.

With respect to printer carriage 4, carriage rail 5, and printer inkjet 6, it is to be understood that, while an ink jet printer is illustrated, other suitable printing devices such as LaserJet printers can also be employed. With this in mind, printer carriage 4 is merely used to assist printer inkjet 6 in placing ink/toner spots 8 and 8' on media 9 and to assist ink/toner spot sensor 10 in monitoring ink/toner spots 8 and 8' in order to determine the dry time profile of ink/toner spots 8 and 8'.

With respect to ink/toner spots 8 and 8', ink/toner spot 8 is an amount of ink/toner placed upon media 9 by printer inkjet 6 such that ink/toner spot sensor 10 is capable of measuring the gloss level of spot 8. Spot 8' is the location of the next site where printer inkjet 6 is likely to place another amount of ink/toner upon media 9.

Media 9, typically, is any suitable material upon which ink/toner spots 8 and 8' can be located and observed by ink/toner spot sensor 10. In this manner, media 9 can be any porous or swellable material upon which an image (spots 8 and 8') can be rendered.

Ink/toner spot sensor 10, preferably, is any suitable sensor technology that is capable of measuring the gloss level of ink/toner spot 8 through the use of specular and diffuse channels or other similar techniques.

Printer controller 12, preferably, is any suitable hardware and/or software device operatively connected to printer carriage 4 in order to increase the printing speed of apparatus 2. Printer speed controller 14, preferably, is operatively connected to printer controller 12 in order to adjust the printing speed of apparatus 2. Ink/toner dry time profile registry 16, preferably, is operatively connected to print controller 12 in order to provide a database in which the ink/toner dry time profiles for a variety of combinations of a particular ink/toner used in combination with a particular media type can be located. It is to be understood that printer speed controller 14 and/or ink/toner dry time profile registry 16 can be located away from printer controller 12. Also, it should be noted that printer speed controller 14 and ink/toner dry time profile registry 16 may be implemented as software modules, hardware units, or a combination of both.

Ink/toner dry time profile registry 16, preferably, contains a database of a variety of previously measured combinations of various media and ink/toner dry time profiles. In this manner, apparatus 2 is capable of matching a particular type of media with the dry time profile of a particular ink/toner.

Figure 2:
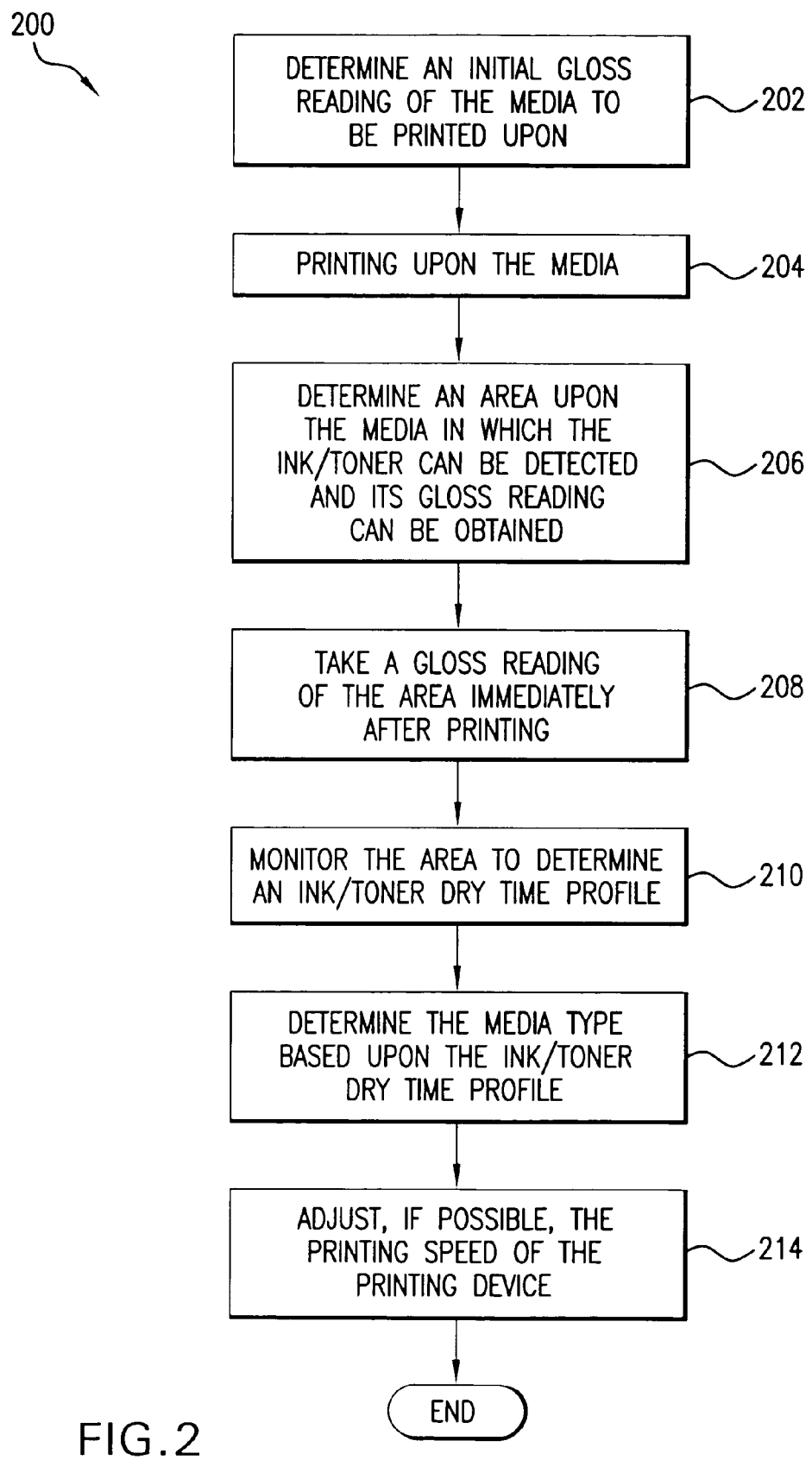
FIG. 2 is a flowchart that illustrates a method for varying printing speed based upon ink/toner dry time profiles, according to another embodiment of the present invention.

With respect to FIG. 2, a method 200 for varying printing speed based upon ink/toner dry time profiles is illustrated. Method 200 includes, in part, the steps of: determining an initial gloss reading of the media 9 (FIG. 1) to be printed upon (step 202); printing upon the media through the use of the printing apparatus 2 (step 204); determining an area upon the media 9 in which the ink/toner spot 8 can be detected and its gloss reading can be obtained (step 206); taking a gloss reading of the ink/toner spot 8 immediately after printing (step 208); monitoring the ink/toner spot 8 in order to determine and ink/toner dry time profile (step 210); determining the media type based upon the ink/toner dry time profile (step 212); and adjusting, if possible, the printing speed of the printing apparatus 2 (step 214).

With respect to step 202, an initial gloss reading of media 9 is to be taken in order to provide a baseline gloss level reading for ink/toner spot sensor 10. This will provide a calibration for ink/toner spot sensor 10.

With respect to steps 206 and 208, ink/toner spot sensor 10 will scan media 9 in order to detect the presence of ink/toner spot 8 and obtain an initial gloss reading ink/toner spot 8.

With respect to step 210, after the initial gloss reading of ink/toner spot 8 has been measured, there are several techniques in which ink/toner spot sensor 10 can obtain subsequent gloss readings of ink/toner spot 8. For example, ink/toner spot sensor 10 can continually monitor ink/toner spot 8 for a desired period of time (from hundreds of milliseconds to a few seconds) and obtain subsequent gloss readings. Also, ink/toner spot sensor 10 can measure the gloss level ink/toner spot 8 while ink/toner spot 8' is being placed upon media 9. It is to be understood that a variety of techniques can be employed to measure the change in the gloss of ink/toner spot 8 in order to assist in determining the media type.

With respect to step 212, after the subsequent gloss reading of ink/toner spot 8 has been obtained, ink/toner dry time profile registry 16 is utilized. In this manner, the ink/toner dry time profile of ink/toner spot 8 is compared with the stored ink/toner dry time profiles located in ink/toner dry time profile registry 16. If a match exists between the actual ink/toner dry time profile and the stored ink/toner dry time profile, a determination can be made as to the type of media upon which ink/toner spot 8 is located. If no match can be obtained and, thus no determination of the media can be obtained, then the default media settings will be used or other well known media determination techniques.

With respect to step 214, after the type of media 9 has been determined, the printing speed of apparatus 2 may be adjusted. For example, if it is determined that media 9 is porous, the printing speed of apparatus 2 may be increased by 50%—depending on printer hardware. Other determinations of the type of media may also allow the printing speed of apparatus 2 to be increased by various percentages.

It is to be understood that the flowchart of FIG. 2 shows the architecture, functionality, and operation of one implementation of the present invention. If embodied in software, each block may represent a module, segment, or portion of code that comprises one or more executable instructions to implement the specified logical function(s). If embodied in hardware, each block may represent a circuit or a number of interconnected circuits to implement the specified logical function(s).

Also, the present invention can be embodied in any computer-readable medium for use by or in connection with an instruction-execution system, apparatus or device such as a computer/processor based system, processor-containing system or other system that can fetch the instructions from the instruction-execution system, apparatus or device, and execute the instructions contained therein. In the context of this disclosure, a "computer-readable medium" can be any means that can store, communicate, propagate or transport a program for use by or in connection with the instruction-execution system, apparatus or device. The computer-readable medium can comprise any one of many physical media such as, for example, electronic, magnetic, optical, electromagnetic, infrared, or semiconductor media. More specific examples of a suitable computer-readable medium would include, but are not limited to, a portable magnetic computer diskette such as floppy diskettes or hard drives, a random access memory (RAM), a read-only memory (ROM), an erasable programmable read-only memory, or a portable compact disc. It is to be understood that the computer-readable medium could even be paper or another suitable medium upon which the program is printed, as the program can be electronically captured, via, for instance, optical scanning of the paper or other medium, then compiled, interpreted or otherwise processed in a single manner, if necessary, and then stored in a computer memory.

Those skilled in the art will understand that various embodiment of the present invention can be implemented in hardware, software, firmware or combinations thereof. Separate embodiments of the present invention can be implemented using a combination of hardware and software or firmware that is stored in memory and executed by a suitable instruction-execution system. If implemented solely in hardware, as in an alternative embodiment, the present invention can be separately implemented with any or a combination of technologies which are well known in the art (for example, discrete-logic circuits, application-specific integrated circuits (ASICs), programmable-gate arrays (PGAs), field-programmable gate arrays (FPGAs), and/or other later developed technologies. In preferred embodiments, the present invention can be implemented in a combination of software and data executed and stored under the control of a computing device.

It will be well understood by one having ordinary skill in the art, after having become familiar with the teachings of the present invention, that software applications may be written in a number of programming languages now known or later developed.

Although the flowchart of FIG. 2 shows a specific order of execution, the order of execution may differ from that which is depicted. For example, the order of execution of two or more blocks may be scrambled relative to the order shown. Also, two or more blocks shown in succession in the FIGURE may be executed concurrently or with partial concurrence. All such variations are within the scope of the present invention.

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. A method for varying a printing speed based upon ink/toner dry time profiles, comprising the steps of:
   determining a gloss reading of an ink/toner located on a media;
   determining an actual ink/toner dry time profile for the media;
   determining the type of media; and
   adjusting, if possible, a printing speed of a printing device that is utilizing the ink/toner.

2. The method, as in claim 1, wherein the gloss reading determining step is further comprised of the steps of:
   determining an initial gloss reading of the media;
   printing upon the media through the use of a printing apparatus;
   determining an area upon the media in which an ink/toner spot can be detected and its gloss reading can be obtained; and
   taking a gloss reading of the ink/toner spot immediately after printing.

3. The method, as in claim 1, wherein the media type determining step is further comprised of the steps of:
   storing a plurality of ink/toner dry time profiles for combinations of various ink/toners and media;
   comparing the actual ink/toner dry time profile with the stored ink/toner dry time profile; and
   determining the type of media from the comparison of the actual versus stored ink/toner dry time profiles.

4. The method, as in claim 1, wherein the printing speed adjusting step is further comprised of the step of:
   increasing the printing speed if it is determined that the media is porous.

5. A program storage medium readable by computer, tangibly embodying a program of instructions executable by the computer to perform method steps for varying a printing speed based upon ink/toner dry time profiles, comprising the steps of:
   determining a gloss reading of an ink/toner located on a media;
   determining an actual ink/toner dry time profile for the media;
   determining the type of media; and
   adjusting, if possible, a printing speed of a printing device that is utilizing the ink/toner.

6. The method, as in claim 5, wherein the gloss reading determining step is further comprised of the steps of:
   determining an initial gloss reading of the media;
   printing upon the media through the use of a printing apparatus;
   determining an area upon the media in which an ink/toner spot can be detected and its gloss reading can be obtained; and
   taking a gloss reading of the ink/toner spot immediately after printing.

7. The method, as in claim 5, wherein the media type determining step is further comprised of the steps of:
   storing a plurality of ink/toner dry time profiles for combinations of various ink/toners and media;
   comparing the actual ink/toner dry time profile with the stored ink/toner dry time profile; and
   determining the type of media from the comparison of the actual versus stored ink/toner dry time profiles.

8. The method, as in claim 5, wherein the printing speed adjusting step is further comprised of the step of:
   increasing the printing speed if it is determined that the media is porous.

9. A printing system for varying a printing speed based upon ink/toner dry time profiles, comprising:
   means for determining a gloss reading of an ink/toner located on a media;
   means for determining an actual ink/toner dry time profile for the media;
   means for determining the type of media; and
   means for adjusting, if possible, a printing speed of a printing device that is utilizing the ink/toner.

10. The method, as in claim 9, wherein the gloss reading determining means is further comprised of:
    means for determining an initial gloss reading of the media;
    means for printing upon the media through the use of a printing apparatus;
    means for determining an area upon the media in which an ink/toner spot can be detected and its gloss reading can be obtained; and
    means for taking a gloss reading of the ink/toner spot immediately after printing.

11. The method, as in claim 9, wherein the media type determining means is further comprised of:
    means for storing a plurality of ink/toner dry time profiles for combinations of various ink/toners and media;
    means for comparing the actual ink/toner dry time profile with the stored ink/toner dry time profile; and
    means for determining the type of media from the comparison of the actual versus stored ink/toner dry time profiles.

12. The method, as in claim 9, wherein the printing speed adjusting means is further comprised of:
    means for increasing the printing speed if it is determined that the media is porous.

* * * * *